US012763181B1

(12) United States Patent
Makarskyy et al.

(10) Patent No.: US 12,763,181 B1
(45) Date of Patent: Oct. 13, 2026

(54) NARRATIVE BASED ELECTRONIC PRESCRIBING

(71) Applicant: Allscripts Software, LLC, Raleigh, NC (US)

(72) Inventors: Stanislav Makarskyy, Buffalo Grove, IL (US); Ethan O'Brien, Raleigh, NC (US); Mark Gregory Plunkett, Libertyville, IL (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 0 days.

(21) Appl. No.: 18/665,509

(22) Filed: May 15, 2024

(51) Int. Cl.
*G16H 20/10* (2018.01)
*G16H 10/60* (2018.01)

(52) U.S. Cl.
CPC ............. *G16H 20/10* (2018.01); *G16H 10/60* (2018.01)

(58) Field of Classification Search
CPC ............................... G16H 20/10; G16H 10/60
See application file for complete search history.

(56) References Cited

PUBLICATIONS

A. Flynn et al., An Experiment to Convert Structured Product Labels into Computable Prescribing Information, (Year: 2021).*
B. Radovic, Integration between electronic prescribing system and pharmacy information system using FHIR standard (Year: 2019).*
C. Romanelli et al., The use of narrative electronic prescribing instructions in pharmacoepidemiology: A scoping review for the International Society for Pharmacoepidemiology (Year: 2021).*

* cited by examiner

*Primary Examiner* — Chinyere Mpamugo
(74) *Attorney, Agent, or Firm* — Calfee, Halter & Griswold LLP

(57) ABSTRACT

Described herein are various technologies pertaining to an improved electronic health records application (EHR) that is configured to facilitate construction and transmittal of an electronic prescription based upon a narrative set forth by a clinician. The improved EHR can allow for the electronic prescription to be generated and transmitted with a single click.

20 Claims, 4 Drawing Sheets

NARRATIVE BASED ELECTRONIC PRESCRIBING

BACKGROUND

Electronic health record applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

A conventional EHR often includes modules that are configured to perform certain functions of the EHR. For instance, a conventional EHR may include a module for obtaining and displaying radiographs, a module for entering prescriptions, a module for transmitting prescriptions to a pharmacy, a module for billing insurance companies, a module for scheduling (which can include scheduling time, reserving rooms, etc.), amongst other modules. Conventional EHRs, however, are currently ill-equipped to assist healthcare workers with prescription data entry. For example, conventional prescription data entry workflow solutions of EHRs are primarily focused on attempts to suggest medication to be prescribed based on, e.g., frequency of prescriptions (i.e., most-frequently prescribed medications), provider prescribing history, patient prescription history, a "favorites" list manually populated by a provider or staff member (e.g., based on diagnosis, specialty, office location, or the like), etc. In these scenarios, the EHR distracts the provider from the context of a particular patient's treatment conversation. The EHR requires that the provider execute many clicks, screen navigations, and even mental calculations when evaluating medication refills and the like. Providers know what they want to prescribe, so burdensome screen navigation and data entry required by conventional EHRs become an impediment to patient treatment.

Conventional EHRs (and standalone or embedded electronic prescription modules) require healthcare workers (e.g., physicians, hospital administrators, etc.) to manually enter each piece of prescription information individually, which is burdensome, error-prone, and not well-suited for streamlining prescription generation. Conventional approaches to computer-based prescription generation implemented by existing EHRs and have not adequately addressed these problems.

In a specific example, historically, an EHR, when employed by a clinician to generate an electronic prescription, operates as follows: 1) the EHR receives text entry in a first field that is used to search for a medication, and searches for medication (typically using a partial match)—the EHR then receives a selection of the medication from the clinician; 2) the EHR receives input from the clinician in a second field that identifies a dispensed quantity (e.g., number of tablets, capsules, films, etc.); 3) the EHR receives input from the clinician in a third field that identifies a dispense unit (e.g., tablet, dispense pack, film, etc.); 4) the EHR receives input from the clinician in a fourth field that identifies a number of days of supply of the medication (e.g., typically less than or equal to 30 days or 90 days); 5) the EHR receives input from the clinician in a fifth field as to the SIG (e.g., take 1 tablet by mouth daily, chew 1 tablet by mouth every day, etc.); 6) the EHR receives input from the clinician in a sixth field as to a number of refills—the clinician typically must compute refills based upon a length of time that the patient is to take the medication; 7) the EHR receives input from the clinician in a seventh field as to a pharmacy where the prescription is to be filled-in some cases, the EHR receives multiple pharmacy selections from the clinician so that the clinician can review real-time pricing information pertaining to the medication at different pharmacies; 8) the EHR receives confirmation that the electronic prescription is to be sent to the pharmacy. In some EHRs, each of the fields mentioned above is presented on a different screen, thereby requiring a client application to generate and display numerous different screens in the course of assisting with generating an electronic prescription. Therefore, the EHR requires numerous clicks, screen navigations, and some mental calculations, despite the clinician knowing exactly what they want to prescribe (and thus the clinician is fighting the EHR to cause the EHR to generate the electronic prescription for the medication).

SUMMARY

The following is a brief summary of subject matter that is described in greater detail herein. This summary is not intended to be limiting as to the scope of the claims.

Described herein are various technologies pertaining to an EHR that is configured with electronic prescribing functionality (or a standalone electronic prescription application) that is configured to perform predictive, narrative based electronic prescription (e.g., generate a "script") generation. Efficient electronic prescribing workflow is a hallmark of any EHR. With ever-changing regulatory requirements, prescription data entry generation by way of an EHR, for example, often becomes an arduous many-click process. Conventional EHRs have been configured to improve the electronic prescribing experience for a user through use of prescription history to suggest prescription attributes, manual configuration to construct a "quick list" of prepopulated prescriptions to avoid repetitive data entry, etc. In order to improve the prescription experience for the user, in one embodiment, an EHR is configured to perform a streamlined prescribing workflow, where a provider can narrate relevant prescription information to the EHR. The narrated prescription information can be typed, written, or spoken, and the EHR translates the narrated prescription information into a set of fully populated user interface (UI) elements that are reviewable by the clinician, thereby reducing a number of screens and/or user clicks required when generating and sending an electronic prescription to a pharmacy down to a single screen and a single click. Practically, this reduces a number of screens that are shown to a clinician when compared to previous approaches, thereby potentially allowing for more individuals to receive care over some time window (e.g., the clinician can provide care to an additional patient per day).

A conventional EHR includes a form that has several key fields (shown on several different screens) to be populated by a healthcare practitioner who is using the EHR, where the fields are to be populated in order to create an electronic prescription to be electronically sent to a pharmacy. These fields include but are not limited to medication name, strength, dosage, quantity, dispense as written (DAW) indicator, SIG (which includes codes for instructions for taking prescribed medications, such as "q" for "every hour"), start date, number of refills, etc. "SIG" is an abbreviation of the Latin "signetur," which means "let it be labeled" and refers to the dosage, administration, etc., instructions for the patient. This results in prescription data entry by way of the EHR being a labor-intensive, multi-screen task. However, even though there are many fields, values of some of the fields can be inferred by the EHR from provider prescribing history, patient prescription history, previously configured templates, the medication itself, etc.

In one embodiment, a user (e.g., prescribing clinician) navigates to an EHR user interface for a given patient. The user sets forth a narrative-based prescription, where the narrative-based prescription can be set forth orally (e.g., a microphone of a computing device captures the narrative-based prescription), set forth by text in a text entry field shown in the EHR user interface, or set forth in handwriting by way of a touch-sensitive display. The narrative-based prescription can include an identity of a medication to be prescribed, a delivery method, a dosage amount and unit of measure, a route of administration, a dosage frequency, a duration, supply, refill quantity, etc. For example, the narrative-based prescription is "Take one 20 mg lisinopril tablet by mouth once a day for 20 days." In another example, the narrative-based prescription is: "Take two 20 mg Lipitor tablets by mouth twice daily for 6 months."

The EHR converts the narrative-based prescription to computer-readable text (e.g., through voice to text technology, handwriting technology, etc.) if required, and the narrative-based prescription is provided to a narrative processor that parses the narrative-based prescription to identify individual portions therein and generates a structured electronic prescription based upon the parsed narrative-based prescription. In an example, the narrative processor can employ a set of rules in connection with identifying the different portions of the narrative-based prescription. In another example, the narrative processor can utilize artificial intelligence (AI) technologies in connection with identifying different portions of the narrative-based prescription. Continuing with one of the examples set forth above, the narrative processor identifies "Take" as the dose delivery method, identifies "one tablet" as the dosage and unit of measure, identifies "20 mg" as the dosage strength, identifies "lisinopril" as the medication, identifies "by mouth" as the route of administration, identifies "once a day" as the dosage frequency, and identifies "for 20 days" as the duration/day's supply/refill quantity.

The discrete elements are then passed to a script (prescription) composer component of the narrative processor. The script composer component generates a structured script response that comprises the discrete element information, where the discrete elements are arranged in a predefined order and standardized. The script composer component can employ a set of rules to generate the structured script response.

In the case where the narrative-based prescription includes SIG codes, the script composer component can convert the SIG codes to natural language (e.g., by performing a table lookup or the like). For example, the user may enter SIG codes such as "Take 2 po tid", and the script composer can translate these instructions to a human-readable, natural language format that reads "Take 2 by mouth 3 times daily".

In another embodiment, the script composer communicates with one or more pricing partners to identify a most economical quantity and dosage of the medication(s) being prescribed (e.g., based upon the structured electronic prescription). For instance, a query can be constructed based upon the structured prescription, where the query includes an identifier of a medication and optionally other information. The query can be transmitted, via various application programming interfaces (APIs), to the pricing partners. The pricing partners return pricing information with respect to the medication identified in the query, equivalents thereof, etc. In an example, information from the pricing partner may indicate that 40 doses of the same medication at 10 mg is cheaper than 20 doses at 20 mg. In this case, the script composer component can select the dosage and quantity that results in most savings to the patient, and constructs and returns a structured electronic prescription to the EHR. The EHR populates editable fields with content of the structured electronic prescription; the user can review and edit the content in the fields prior to submitting the electronic prescription to the appropriate pharmacy (e.g., identified when querying the pricing partners). From the foregoing, then, the user can set forth a narrative-based prescription, and fields in the EHR interface are populated with values that are based upon the narrative-based prescription, where the values correspond to the most economical pricing for the patient to whom medication is being prescribed. The clinician reviews such values, edits values when necessary, and submits the electronic prescription. Therefore, rather than an EHR forcing the clinician to navigate through several screens, input individual values, compute dosages, and so forth, the EHR described herein facilitates one-click prescribing, where the final electronic prescription is generated based upon most advantageous pricing information (from the perspective of the patient) from pricing partners.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
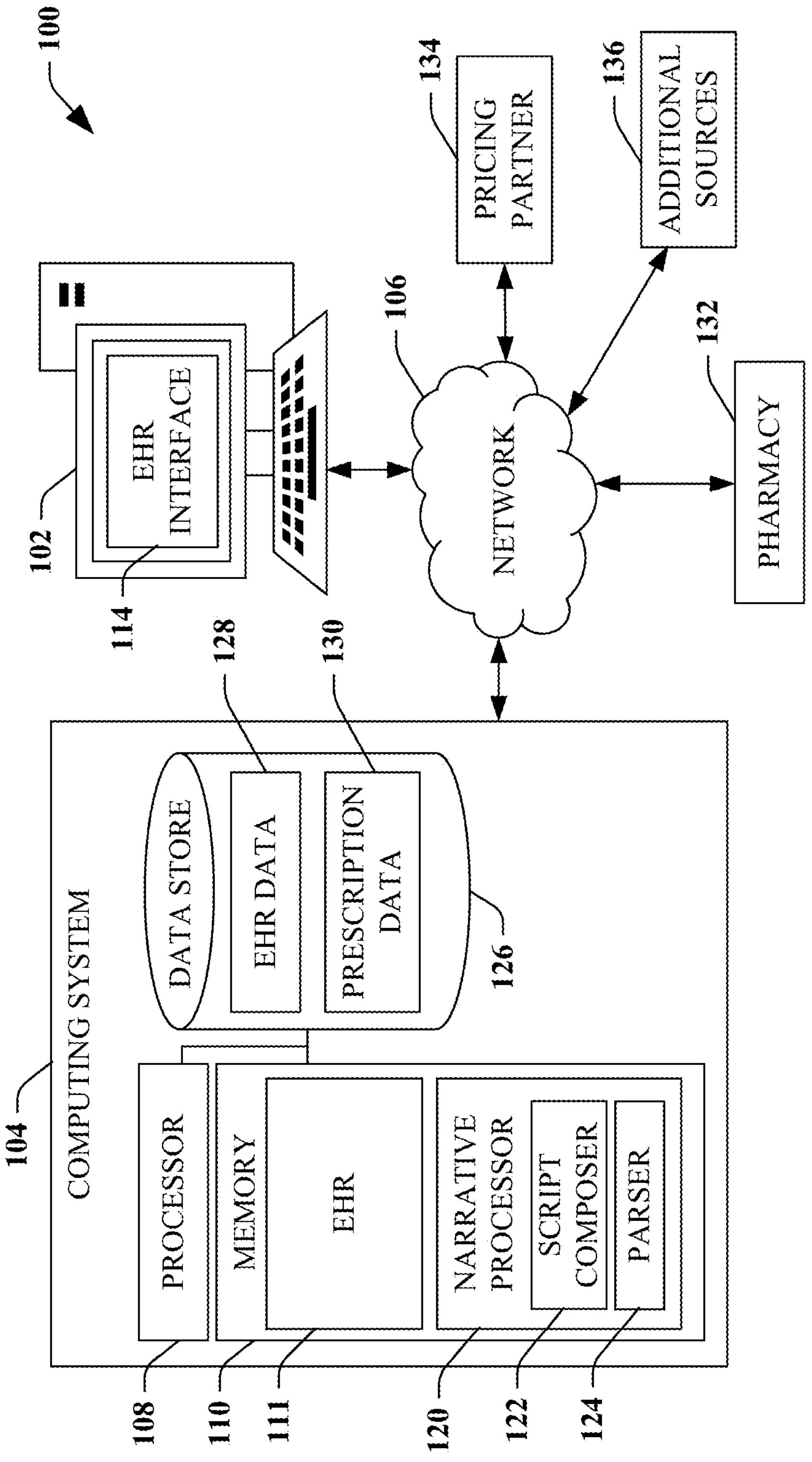
FIG. 1 illustrates an exemplary system that facilitates narrative-based prescription generation and reduces an amount of data entry required by a user when generating a prescription.

Various technologies pertaining to an improved EHR that provides functionality related to predictive, narrative-based prescription generation are described herein. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something and is not intended to indicate a preference.

Historically, an EHR receives a request from a clinician to navigate to a prescription user interface to prescribe a medication, whereupon the EHR provides text entry fields (potentially on different screens) that are configured to receive manually generated values from the clinician, often requiring numerous screen refreshes and clicks. The described systems and methods relate to an improved EHR that reduces an amount of data entry of the clinician and time that the clinician must spend in the prescription user interface, which in turn increases the amount of time that the clinician can spend in providing care to patients of the clinician.

Described herein are various technologies pertaining to predictive, narrative-based prescription generation. With regard to EHRs, prescription data entry is regulated by the industry and therefore is similar across different EHR software vendors. In general, an EHR prescription generation screen allows the clinician to perform certain actions such as searching for a medication to be prescribed, entering a dispense quantity, entering a dispense unit, entering a number of days' supply, entering prescription instructions or "SIG" codes as they are sometimes referred to herein, entering a number of refills, selecting a pharmacy, and finally sending the prescription to the pharmacy (where the EHR may provide such functionality across several screens). Receiving a dispensed quantity involves receiving a number of tablets, capsules, films, milliliters, etc. Receiving a dispense unit involves receiving an indication of the type of medication (e.g., tablet, capsule, film, etc.). With respect to the number of days' supply, the EHR receive a number (e.g., 10, 30, 90, etc.) optionally with a remainder allocated for refills.

The EHR can also receive one or more SIG codes, which are then used by a pharmacy to print instructions to the user. SIG codes indicate medication dosages, measurements, dosage times or frequency, routes of administration, etc. The SIG code can be translated to, e.g., "take 1 tablet by mouth daily," or "take one tablet by mouth twice daily with food," etc. The EHR can also receive refill information, which often requires a calculation by the clinician based on how long the patient should take the medication. The EHR can receive a user selection of a pharmacy and, in some cases, receive a modification of the pharmacy selection based on real time pricing information for the medication. Finally, the EHR sends the script to the pharmacy.

According to various aspects described herein, an improved EHR that provides an improvement to the above-referenced electronic prescribing workflow is provided. Using the described approach, the EHR significantly reduces an amount of required user data entry, resulting in a more efficient and expedient prescribing workflow. Moreover, the improved EHR displays fewer screens than conventional EHRs, and further requires fewer user clicks to complete an electronic prescription. In this manner, clinicians can dedicate more time to patient care as opposed to navigating screens of an EHR.

With reference now to FIG. 1, an exemplary system 100 is illustrated that facilitates narrative-based prescription generation to reduce an amount of data entry required by a user when generating an electronic prescription. A client device 102 is connected to a computing system 104 via a network 106. In another embodiment, one or more of the components shown in the computing system 104 can reside on the client device 102. The computing system 104 comprises a processor 108 that executes, and a memory 110 that stores, computer-executable instructions for performing various acts that facilitate providing the functionality described herein. The memory 110 also stores an electronic health records application (EHR) 111. While not illustrated, the EHR 111 can be a distributed application that is executed by multiple different computing systems. For instance, the EHR 111 can include an EHR frontend and an EHR backend, where the EHR frontend and EHR backend are executed on different computing systems. Additionally, the EHR backend can include a service layer, which is a set of components that facilitates searching database(s) for particular information. The EHR frontend is configured to construct an EHR user interface 114 and cause the EHR user interface 114 to be displayed on a display of the client device 102 (e.g., by way of a client-side application, such as a web browser, an application dedicated to the EHR 111, etc.).

The memory 110 additionally includes a narrative processing component 120 that facilitates constructing structured, standardized electronic prescriptions based upon a narrative-based prescription set forth by a clinician who is using the client device 102. The narrative processing component 120 comprises a script composer component 122 and a parser component 124, where operation of the components 122 and 124 will be described in greater detail below. The narrative processor component 120 is depicted as being included in the same memory 110 as the EHR 111 for ease of explanation; in practice, the narrative processor component 120 may be included in a computing system that is separate from the computing system 104.

The EHR interface 114 is presented to the clinician on the client device 102 with respect to generating electronic prescriptions for patients. The clinician interacts with the EHR user interface 114 (e.g., a graphical user interface (GUI) or the like) to view a given patient's electronic health record when generating prescriptions for the patient. The computing system 104 further includes a data store 126 that stores EHR data 128 and prescription data 130 (e.g., historical prescription data, current prescription data, updated prescription data, etc.). When the clinician elects to view a given patient's EHR data 128, the processor 108 accesses the data store 126 to retrieve EHR data 128 for the patient. The EHR data 128 for the patient is presented to the user via the EHR user interface 114. In one embodiment, the computing system 104 is remote from the client device 102 as illustrated in FIG. 1. It will be understood, however, that in other embodiments the computing system 104 maybe integral to the client device 102.

The system 100 additionally includes a pharmacy computing system 132, a pricing partner computing system 134, and computing system(s) of additional source(s) 136, each of which are in communication with the computing system 104 by way of the network 106.

Figure 2:
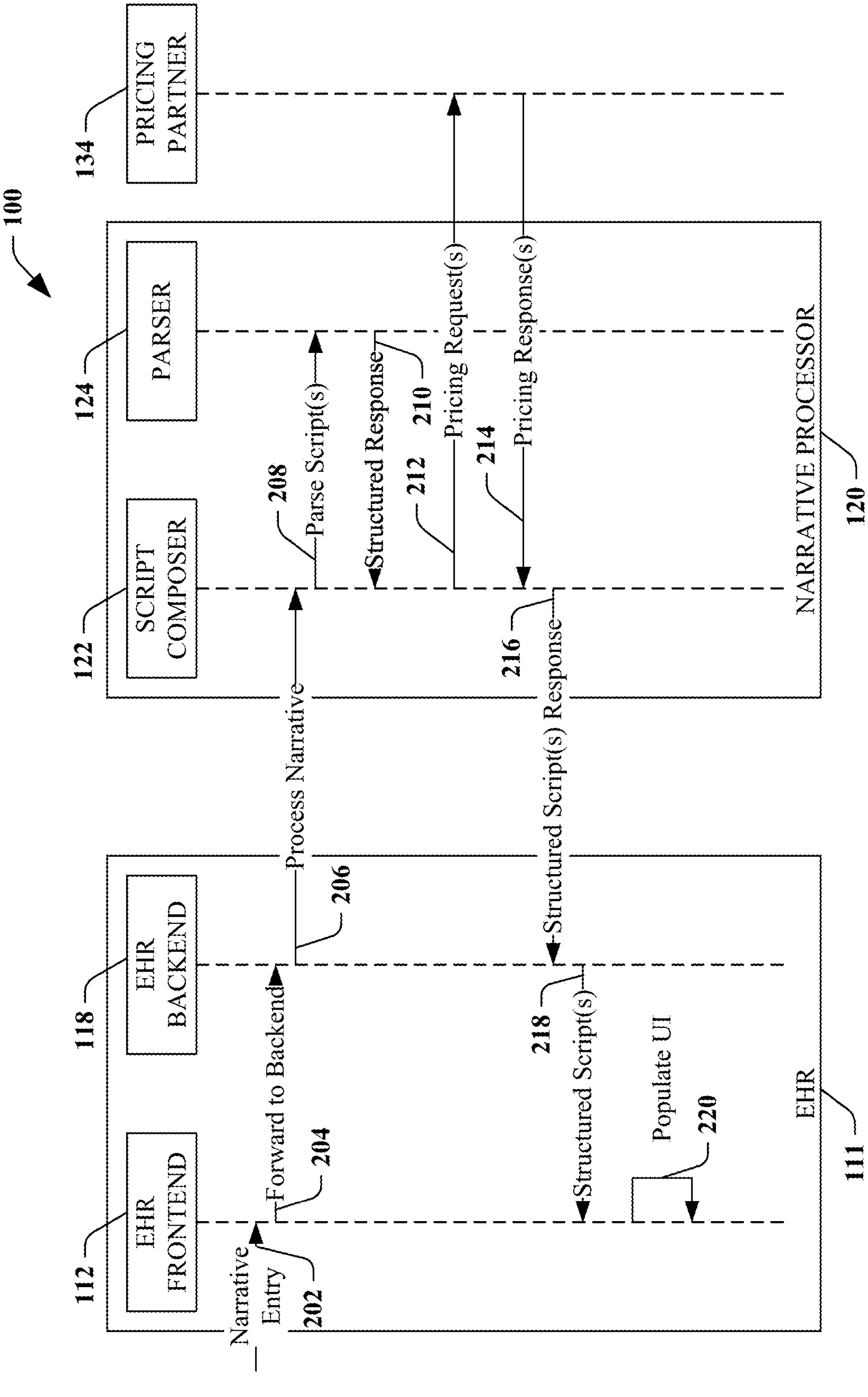
FIG. 2 illustrates a data flow between various components of the EHR front end, back end,, and the narrative processor.

Communications amongst the various devices and components is now described with reference to FIG. 2, where a structured, standardized electronic prescription is constructed based upon a narrative-based prescription. Specifically, FIG. 2 illustrates communications between an EHR frontend 112 of the EHR 111, an EHR backend 118 of the EHR 111, the script composer 122 of the narrative processor component 120, the parser 124 of the narrative processor component 120, and the pricing partner 134.

At 202, a narrative entry (a narrative-based prescription) is received by the EHR frontend 112 from the client device 102, where the client device 102 received the narrative entry from the clinician by way of the EHR interface 114. In an example, the narrative entry is a spoken entry, where a microphone associated with the client device 102 captures the spoken narrative entry and the client device 102 transcribes the narrative entry (through voice to text functionality executed by the client device 102). In another example, the EHR interface 114 includes a text entry field, where the clinician populates the text entry field with the narrative entry. In yet another example, the client device 102 includes a touch-sensitive display, where the clinician handwrites the narrative entry by way of the touch-sensitive display and the client device 102 converts the handwritten narrative entry to computer-readable text. For instance, the narrative entry is "take one 20 mg lisinopril tablet by mouth once a day for 20 days." In another example, the narrative entry is "take two 20 mg Lipitor tablets by mouth twice daily for 6 months." Additionally or alternatively, the narrative entry can include sig codes, which are often used by clinicians to set forth prescription information using a relatively small amount of text.

At 204, the EHR frontend 112 forwards the narrative entry (in the form of computer-readable text) to the EHR backend 118. At 206, narrative processing is initiated, as the EHR backend 118 passes the narrative entry to the script composer 122 of the narrative processor 120. The script composer 122 passes the entered text to the parser component 124 for parsing and identification of discrete prescription elements (medication, dose, strength, frequency, route of administration, etc.) at 208. With more specificity, the parser component 124 receives an unstructured string, parses the string, and identifies discrete elements that correspond to a structured prescription from the string. The parser component 124 can utilize a variety of technologies when mapping text from the unstructured string to the well-defined, structured text. In an example, the parser component 124 utilizes a set of rules to map content from the narrative entry to entries in a structured vector. Hence, the parser component 124 can employ named entity recognition (NER) technologies to extract an identity of a medication from the narrative entry. Moreover, the parser component 124 can utilize rules corresponding to part of speech processing to identify verbs, nouns, pronouns, etc. in the narrative-based entry, and map terms to the structured vector based upon such rules. Additionally or alternatively, the parser component 124 can utilize artificial intelligence (AI) technologies in connection with mapping content of the narrative entry to elements of the structured vector. For instance, the parser component 124 can be or include a large language model LLM, and a prompt can be provided to the LLM that includes the narrative entry as well as an instruction for the LLM to populate the structured vector based upon content of the narrative entry. The parser component 124 can construct a structured response based upon the identified discrete elements, where the structured response includes identifiers of the discrete elements and metadata assigned thereto (e.g., medication identifier, quantity, SIG codes, and so forth).

At 210, the parser component 124 sends a structured response, which comprises the discrete elements that were extracted from the narrative, metadata assigned thereto, and identifiers of any errors found during the parsing operation, to the script composer 122. An example of operation of the parser component 124 with respect to the narrative entry "take 1 tablet 2 times a day for 60 days" is set forth below. In response to receiving such narrative entry, the parser component 124 can return the following structured response:

```
{
  "containsLatinAbbreviations": false,
  "originalSig": " take 1 tablet 2 times a day for 60 days",
  "preprocessedSig": "take 1 tablet 2 times a day for 60 days",
  "maximumDosage": {
    "minDose": 2,
    "maxDose": 2,
    "complex": false,
    "doseUnit": {
      "form": {
        "valueEnums": [
          "Tablet"
        ],
        "index": 7,
        "length": 6,
        "humanReadable": "tablet"
      },
      "index": 7,
      "length": 6,
      "humanReadable": "tablet"
    },
    "index": 0,
    "length": 0,
    "humanReadable": "2 tablets"
  },
  "dosages": [
    {
      "doseDeliveryMethod": {
      "valueEnum": "Take",
      "index": 0,
      "length": 4,
      "humanReadable": "take"
    },
    "dose": {
      "minDose": 1,
      "maxDose": 1,
      "complex": false,
      "doseUnit": {
        "form": {
          "valueEnums": [
            "Tablet"
          ],
          "index": 7,
          "length": 6,
          "humanReadable": "tablet"
        },
        "index": 7,
        "length": 6,
        "humanReadable": "tablet"
      },
      "index": 5,
      "length": 8,
      "humanReadable": "1 tablet"
    },
    "frequency": {
      "containsLatinAbbreviations": false,
```

-continued

```
      "intervals": [
        {
          "containsLatinAbbreviations": false,
          "freq": 2,
          "freqMax": 2,
          "period": 1,
          "periodMax": 1,
          "expressAsPer": false,
          "periodUnit": "Day",
          "inferred": false,
          "maximumDailyFrequency": 2,
          "index": 14,
          "length": 13,
          "humanReadable": "2 times every day"
        }
      ],
      "when": [ ],
      "timeOfDay": [ ],
      "daysOfWeek": [ ],
      "maximumDailyFrequency": 2,
      "index": 14,
      "length": 13,
      "humanReadable": "2 times every day"
    },
    "duration": {
      "count": 60,
      "period": {
        "valueEnum": "Day",
        "index": 0,
        "length": 0,
        "humanReadable": "day"
      },
      "unbounded": false,
      "index": 28,
      "length": 11,
      "humanReadable": "for 60 days"
    },
    "maximumDailyDose": {
      "minDose": 2,
      "maxDose": 2,
      "complex": false,
      "doseUnit": {
        "form": {
          "valueEnums": [
            "Tablet"
          ],
          "index": 7,
          "length": 6,
          "humanReadable": "tablet"
        },
        "index": 7,
        "length": 6,
        "humanReadable": "tablet"
      },
      "index": 0,
      "length": 0,
      "humanReadable": "2 tablets"
    },
    "confidence": "High",
    "confidenceReasons": [ ],
    "index": 0,
    "length": 39,
    "humanReadable": "take 1 tablet 2 times every day for 60 days"
  }
],
  "confidence": "High",
  "confidenceReasons": [ ],
  "index": 0,
  "length": 39,
  "humanReadable": "take 1 tablet 2 times every day for 60 days"
}
```

In another example, the narrative entry may include insufficient data. For instance, the narrative entry can be "take 1 tablet um times a day." The parser component 124 can output the following:

```
{
  "containsLatinAbbreviations": false,
  "originalSig": " take 1 tablet 2 times a day for um days",
  "preprocessedSig": "take 1 tablet 2 times a day for um days",
  "dosages": [ ],
  "confidence": "None",
  "confidenceReasons": [
    "Syntax error: unexpected '<EOF>' at Ln 1, Col 39",
    "Text from the original sig was not parsed: 'take 1 tablet 2 times a
    day for um days'",
    "Not all dosages high confidence"
  ],
  "index": 0,
  "length": 0,
  "humanReadable": ""
}
```

In one embodiment, at 212, the script composer 122, in response to receiving the structured response, generates and transmits a query to the pricing partner 134 by way of an exposed API of the pricing partner 134. The pricing partner 134 may be a pharmacy. In another example, the pricing partner 134 is a clearinghouse. For instance, based upon the structured response, the script composer 122 can extract an identification of medication included in the structured response and construct the query, where the script composer 122 includes the identification of the medication in the query. Optionally, the script composer 122 includes other information in the query, such as dosage, number of days that the medication is to be taken, etc. Once constructed, the parser component 124 transmits the query to the pricing partner 134. The pricing partner 134 transmits a pricing response identifying lowest prices for the medication(s) to the script composer 122, at 214. As indicated previously, the script composer 122 can transmit the query to several pricing partners simultaneously, and thus receive pricing responses from the several pricing partners. Upon receiving the pricing responses, the script composer 122 constructs a structured script response, where the structured script response optionally includes information obtained from the pricing responses. For instance, when the pricing responses indicate that it is more cost effective to acquire medication in 40 mg tablets rather than 20 mg tablets, the structured script response can include an indication that the electronic prescription is for 40 mg tablets (e.g., cut in half) rather than 20 mg tablets.

At 216, the script composer 122 passes the structured script response to the EHR backend 118, where the structured response can be a JSON document, an XML document, etc. At 218, the EHR backend 118 translates the script data to an EHR specific data model, if necessary, and passes the structured script(s) to the EHR frontend 112. Upon receipt of the structured script, the EHR frontend 112, at 220, causes values in the structured script to populate data fields presented on the EHR user interface 114; specifically, the EHR frontend 112 updates the EHR user interface 114 and causes the EHR user interface 114 to be presented on the display of the client device 102.

There are numerous technical advantages associated with the technologies described herein. Rather than the EHR forcing the clinician to manually enter values into different fields, potentially on different screens, and perform mental computations when constructing an electronic prescription, the improved EHR described herein is configured to receive a narrative-based prescription and populate data fields on a single screen for review and approval by the clinician. Therefore, in some instances, the EHR allows the clinician to generate an electronic prescription and transmit the electronic prescription to a pharmacy with a single click. In turn, as a practical matter, the clinician (and other clinicians using the EHR) can provide care to more patients than previously possible. Moreover, the improved EHR is configured to automatically identify medication(s), strengths, dosage amounts, etc. that result in optimal economic benefit to the patient.

Figure 3:
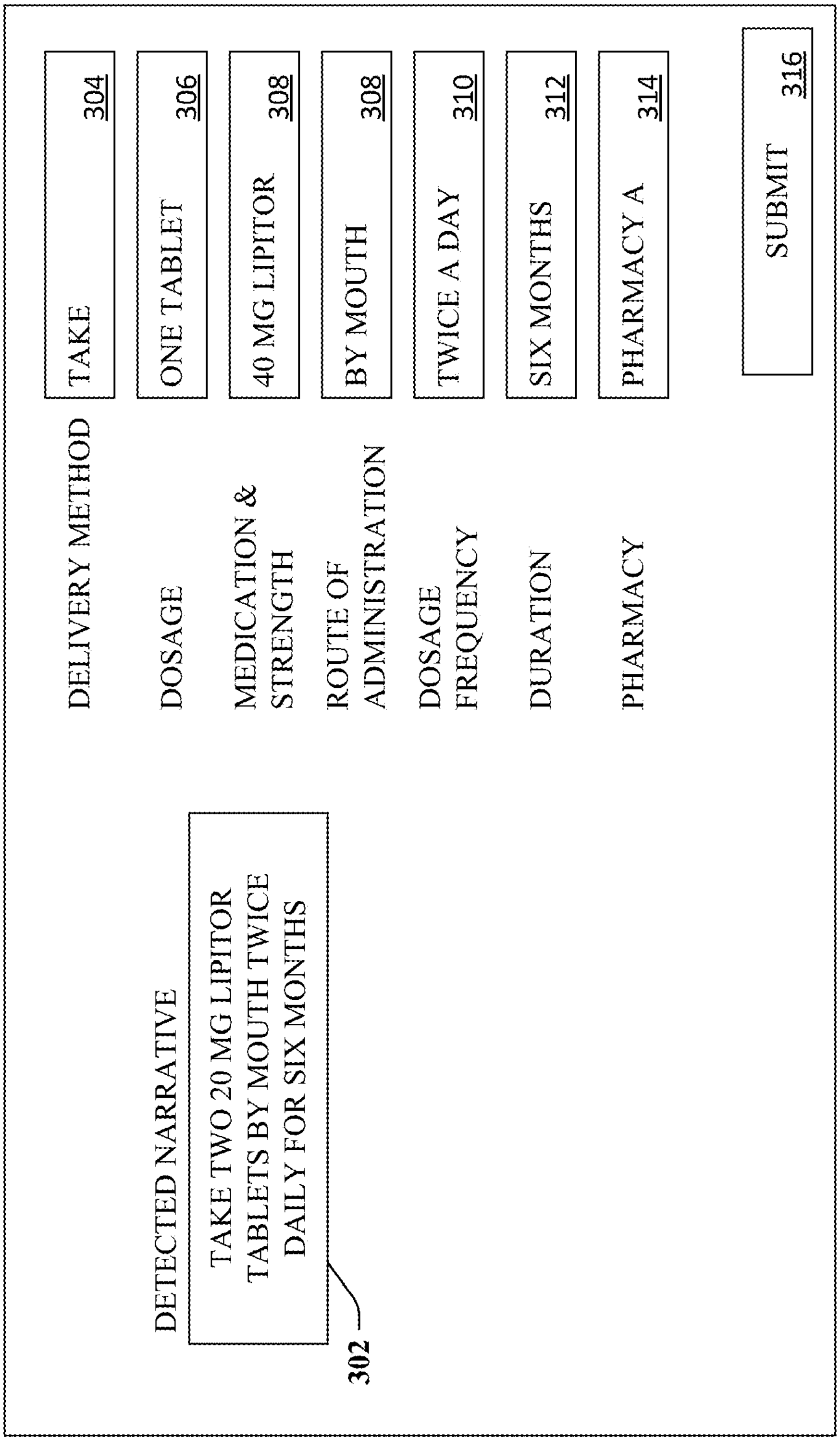
FIG. 3 illustrates an example of an EHR user interface page.

FIG. 3 depicts an example of the EHR interface 114 depicted on the client device. In the example EHR interface 114 depicted in FIG. 3, the interface 114 includes a field 302 that depicts the narrative-based prescription set forth by the clinician. The field 302 can be editable; for instance, voice to text technology may incorrectly transcribe a spoken utterance of the clinician. The EHR can receive edits to the narrative-based prescription by way of the field 302, such that the narrative-based prescription is correct from the perspective of the clinician. When content of the field 302 is edited, values in other fields included in the EHR interface 114 are automatically updated.

As discussed above, the narrative-based prescription (shown in the field 302) is transformed into a structured electronic prescription, and discrete elements are extracted from the narrative-based prescription. Fields 304-316 are populated with the discrete elements extracted from the narrative-based prescription depicted in the field 302. For instance, the field 304 depicts a delivery method extracted from the narrative; field 306 depicts a dosage obtained from the narrative; field 308 depicts an identity of a medication and strength of such medication obtained from the narrative; field 310 depicts a route of administration obtained from the narrative; field 312 depicts a dosage frequency obtained from the narrative; field 314 depicts a duration obtained from the narrative; and field 316 depicts a pharmacy where the electronic prescription is to be submitted. In an example, the pharmacy can be extracted from a profile of a patient (e.g., a preferred pharmacy). In another example, an identity of the pharmacy can be obtained based upon information received from a pricing partner, as described above. It can be ascertained that the element in the fields 306 and 308 do not precisely match content of the narrative shown in the field 302; however, the values in the fields 306 and 308 are functionally equivalent to the elements in the narrative, and are automatically generated based upon real-time information received from pricing partners.

The fields 304-316 are editable by the clinician; for instance, the clinician can alter the duration from six months to some other period by editing content of the field 314. Upon reviewing and approving content of the fields 304-316, a submit button 318 can be selected by the clinician, and the electronic prescription is transmitted to the pharmacy identified in the field 316.

Figure 4:
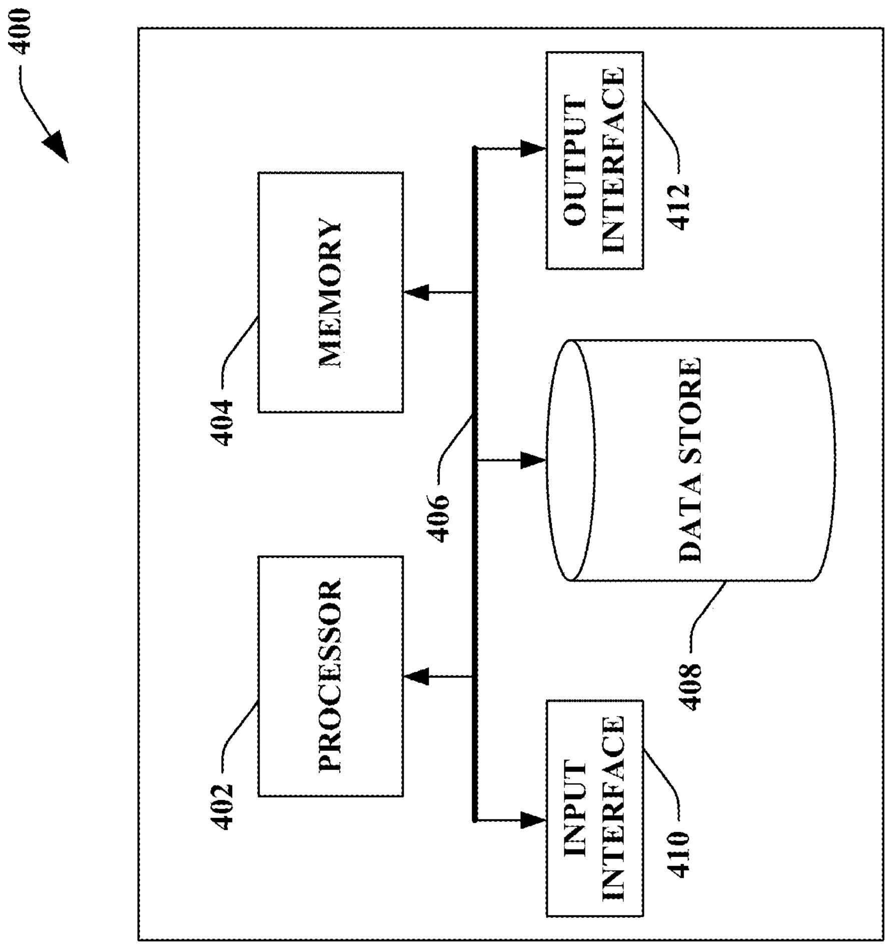
FIG. 4 is a high-level illustration of an exemplary computing device that can be used in accordance with the systems and methodologies disclosed herein is illustrated.

Referring now to FIG. 4, a high-level illustration of an exemplary computing device 400 that can be used in accordance with the systems and methodologies disclosed herein is illustrated. For instance, the computing device 400 may be used in a system that facilitates predictive narrative prescribing of medications, such as the computing system 104 of FIG. 1. The computing device 400 includes at least one processor 402 that executes instructions that are stored in a memory 404. The instructions may be, for instance, instructions for implementing functionality described as being carried out by one or more components discussed above or instructions for implementing one or more of the methods described above. The processor 402 may access the memory 404 by way of a system bus 406. In addition to storing executable instructions, the memory 404 may also store prescription data for the healthcare worker and/or patient(s).

The computing device 400 additionally includes a data store 408 that is accessible by the processor 402 by way of the system bus 406. The data store 408 may include executable instructions, patient data, prescription data, prescriber data, EHR data, etc. The computing device 400 also includes an input interface 410 that allows external devices to communicate with the computing device 400. For instance, the input interface 410 may be used to receive instructions from an external computer device, from a user, etc. The computing device 400 also includes an output interface 412 that interfaces the computing device 400 with one or more external devices. For example, the computing device 400 may display text, images, etc. by way of the output interface 412.

It is contemplated that the external devices that communicate with the computing device 400 via the input interface 410 and the output interface 412 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, microphone, remote control, or the like and provide output on an output device such as a display. Further, a natural user interface may enable a user to interact with the computing device 400 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 400 may be a distributed system. Thus, for instance, several devices may be in communication by way of a network connection and may collectively perform tasks described as being performed by the computing device 400.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computing system comprising:

a processor; and memory storing instructions that, when executed by the processor, cause the processor to perform acts comprising:

receiving computer-readable text from a backend of an electronic health records application (EHR), where the computer-readable text represents a prescription set forth by a clinician in an unstructured narrative form;

providing the computer-readable text as input into a computer-implemented parser model, wherein the computer implemented parser model is configured to parse the computer-readable text and generate an output comprising discrete elements of the prescription from the computer-readable text;

subsequent to obtaining the output generated by the computer-implemented parser model, constructing a structured prescription based upon the output generated by the computer-implemented parser model, where the structured prescription has a standardized format, and further where the structured prescription includes a subset of the discrete elements extracted from the computer-readable text; and transmitting the structured prescription to the backend of the EHR, where the EHR populates several editable fields of a prescription generation interface of the EHR with values based upon the structured prescription, and further where the EHR transmits an electronic prescription to a pharmacy upon receipt of an indication that a clinician has accepted the values in the editable fields.

2. The computing system of claim 1, where the structured prescription is a JSON data structure.

3. The computing system of claim 1, where the structured prescription is an XML data structure.

4. The computing system of claim 1, where the several editable fields are configured to present values for delivery method of a medication, dosage of the medication, type of the medication, strength of the medication, route of administration, dosage frequency, duration, and pharmacy, respectively.

5. The computing system of claim 1, the acts further comprising:

using speech to text functionality to transcribe a spoken utterance of the clinician to the computer-readable text.

6. The computing system of claim 1, the acts further comprising:

generating a query based upon the parsing of the computer-readable text, where the query includes an identification of a medication;

transmitting the query to a computing system of a pricing partner, where the computing system of the pricing partner identifies pricing information pertaining to the medication based upon the query;

receiving the pricing information from the computing system of the pricing partner, where the structured prescription is constructed based upon the pricing information.

7. The computing system of claim 6, where the structured prescription includes a value that is based upon a first discrete element in the discrete elements but differs from the first discrete element in the discrete elements.

8. A method performed by a computing system, the method comprising:

receiving computer-readable text from a backend of an electronic health records application (EHR), where the computer-readable text represents a prescription set forth by a clinician in an unstructured narrative form;

providing the computer-readable text as input into a computer-implemented parser model, wherein the computer implemented parser model is configured to parse the computer-readable text and generate an output comprising discrete elements of the prescription from the computer-readable text;

subsequent to obtaining the output generate by the computer-implemented parser model, constructing a structured prescription based upon the output generated by the computer-implemented parser model, where the structured prescription has a standardized format, and further where the structured prescription includes a subset of the discrete elements extracted from the computer-readable text; and transmitting the structured prescription to the backend of the EHR, where the EHR populates several editable fields of a prescription generation interface of the EHR with values based upon the structured prescription, and further where the EHR transmits an electronic prescription to a pharmacy upon receipt of an indication that a clinician has accepted the values in the editable fields.

9. The method of claim 8, where the structured prescription is a JSON data structure.

10. The method of claim 8, where the structured prescription is an XML data structure.

11. The method of claim 8, where the several editable fields are configured to present values for delivery method of a medication, dosage of the medication, type of the medication, strength of the medication, route of administration, dosage frequency, duration, and pharmacy, respectively.

12. The method of claim 8, further comprising:

using speech to text functionality to transcribe a spoken utterance of the clinician to the computer-readable text.

13. The method of claim 8, further comprising:

generating a query based upon the parsing of the computer-readable text, where the query includes an identification of a medication;

transmitting the query to a computing system of a pricing partner, where the computing system of the pricing partner identifies pricing information pertaining to the medication based upon the query;

receiving the pricing information from the computing system of the pricing partner, where the structured prescription is constructed based upon the pricing information.

14. The method of claim 13, where the structured prescription includes a value that is based upon a first discrete element in the discrete elements but differs from the first discrete element in the discrete elements.

15. A non-transitory computer-readable storage medium storing instructions that, when executed by a processor, cause the processor to perform acts comprising:

receiving computer-readable text from a backend of an electronic health records application (EHR), where the computer-readable text represents a prescription set forth by a clinician in an unstructured narrative form;

providing the computer-readable text as input into a computer-implemented parser model, wherein the computer implemented parse model is configured to parse the computer-readable text and generate an output comprising discrete elements of the prescription from the computer-readable text;

subsequent to obtaining the output generate by the computer-implemented parser model, constructing a structured prescription based upon the output generated by the computer-implemented parser model, where the structured prescription has a standardized format, and further where the structured prescription includes a subset of the discrete elements extracted from the computer-readable text; and transmitting the structured prescription to the backend of the EHR, where the EHR populates several editable fields of a prescription generation interface of the EHR with values based upon the structured prescription, and further where the EHR transmits an electronic prescription to a pharmacy upon receipt of an indication that a clinician has accepted the values in the editable fields.

16. The computer-readable storage medium of claim 15, where the structured prescription is a JSON data structure.

17. The computer-readable storage medium of claim 15, where the structured prescription is an XML data structure.

18. The computer-readable storage medium of claim 15, where the several editable fields are configured to present values for delivery method of a medication, dosage of the medication, type of the medication, strength of the medication, route of administration, dosage frequency, duration, and pharmacy, respectively.

19. The computer-readable storage medium of claim 15, further comprising:

using speech to text functionality to transcribe a spoken utterance of the clinician to the computer-readable text.

20. The computer-readable storage medium of claim 15, further comprising:

generating a query based upon the parsing of the computer-readable text, where the query includes an identification of a medication;

transmitting the query to a computing system of a pricing partner, where the computing system of the pricing partner identifies pricing information pertaining to the medication based upon the query;

receiving the pricing information from the computing system of the pricing partner, where the structured prescription is constructed based upon the pricing information.

* * * * *